US00PP21838P2

(12) United States Plant Patent
Warren

(10) Patent No.: US PP21,838 P2
(45) Date of Patent: Apr. 5, 2011

(54) MAPLE TREE NAMED 'JFS-KW202'

(50) Latin Name: *Acer truncatum*
Varietal Denomination: JFS-KW202

(75) Inventor: Keith S. Warren, Gresham, OR (US)

(73) Assignee: J. Frank Schmidt & Son Co., Boring, OR (US)

( * ) Notice: Subject to any disclaimer, the term of this patent is extended or adjusted under 35 U.S.C. 154(b) by 10 days.

(21) Appl. No.: 12/462,215

(22) Filed: Jul. 30, 2009

(51) Int. Cl.
*A01H 5/00* (2006.01)

(52) U.S. Cl. ..... Plt./224

(58) Field of Classification Search ..... Plt./224
See application file for complete search history.

(56) References Cited

U.S. PATENT DOCUMENTS

| | | | | |
|---|---|---|---|---|
| PP735 P | | 1/1946 | Barbier | |
| PP7,433 P | * | 1/1991 | Warren | Plt./224 |
| PP7,529 P | | 5/1991 | Warren | |
| PP17,367 P3 | | 1/2007 | Johansson | |
| PP20,109 P3 | | 6/2009 | Worthington | |

* cited by examiner

*Primary Examiner*—Wendy C. Haas
(74) *Attorney, Agent, or Firm*—Klarquist Sparkman, LLP

(57) ABSTRACT

A new variety of maple tree that combines deep purple summer foliage with a slightly compact, upright growth habit and improved heat resistance in comparison to other maple trees with purple colored summer foliage.

11 Drawing Sheets

Latin name of the genus and species of the plant claimed: *Acer truncatum.*

Variety denomination: 'JFS-KW202'.

BACKGROUND OF THE INVENTION

In 1983, I became interested in selecting new tree cultivars from the species *Acer truncatum*. I collected seed, and in the summer of 1984, I grew a group of seedlings in a seed lot. Although the pollen parent of these seedlings was unknown, observation of foliage and growth made me think that the pollen parent was *Acer platanoides*. I planted out the 50 strongest of the seedlings from this seed lot for evaluation and to facilitate cross pollination to create seed for possible future selection. From these 50 selected seedlings, I later selected and patented two cultivars, 'Warrenred' U.S. Plant Pat. No. 7,433 and 'Keithsform' U.S. Plant Pat. No. 7,529.

Over the next several years, I selected additional seedlings of *Acer truncatum* from a variety of different sources and added the best specimens to my evaluation and cross pollination plot. These trees were allowed to grow to the size at which they would set seed. I allowed all of these trees to cross pollinate, and I collected seed from the best looking trees in the plot. I germinated the seed in seedbeds and grew thousands of seedlings for evaluation. Among these open pollinated seedlings, in 1997, I noticed that several of my plants displayed some degree of purple leaf coloration. In the spring of 1998, I transplanted these trees to a row in Boring, Oreg. I selected one particular seedling in the summer of 1998 that had particularly deep purple foliage, that I have now named 'JFS-KW202'.

Realizing that this seedling tree possessed unique characteristics, I grew this tree to more mature size and repeatedly propagated small plots of this tree vegetatively by T-budding onto *Acer platanoides* rootstock and by softwood cuttings. From this propagation, I found that the characteristics of my new tree were indeed unique and were firmly fixed.

BRIEF SUMMARY OF THE INVENTION

This new cultivar possesses a unique combination of characteristics in that it combines deep purple summer foliage with a slightly compact, upright growth habit and better heat resistance in comparison to other maple trees with purple foliage of which I am aware.

BRIEF DESCRIPTION OF THE DRAWING

The colors of an illustration of this type may vary with lighting conditions and, therefore, color characteristics of this new variety should be determined with reference to the observations described herein, rather than from these illustrations alone.

DETAILED BOTANICAL DESCRIPTION

Figure 1:
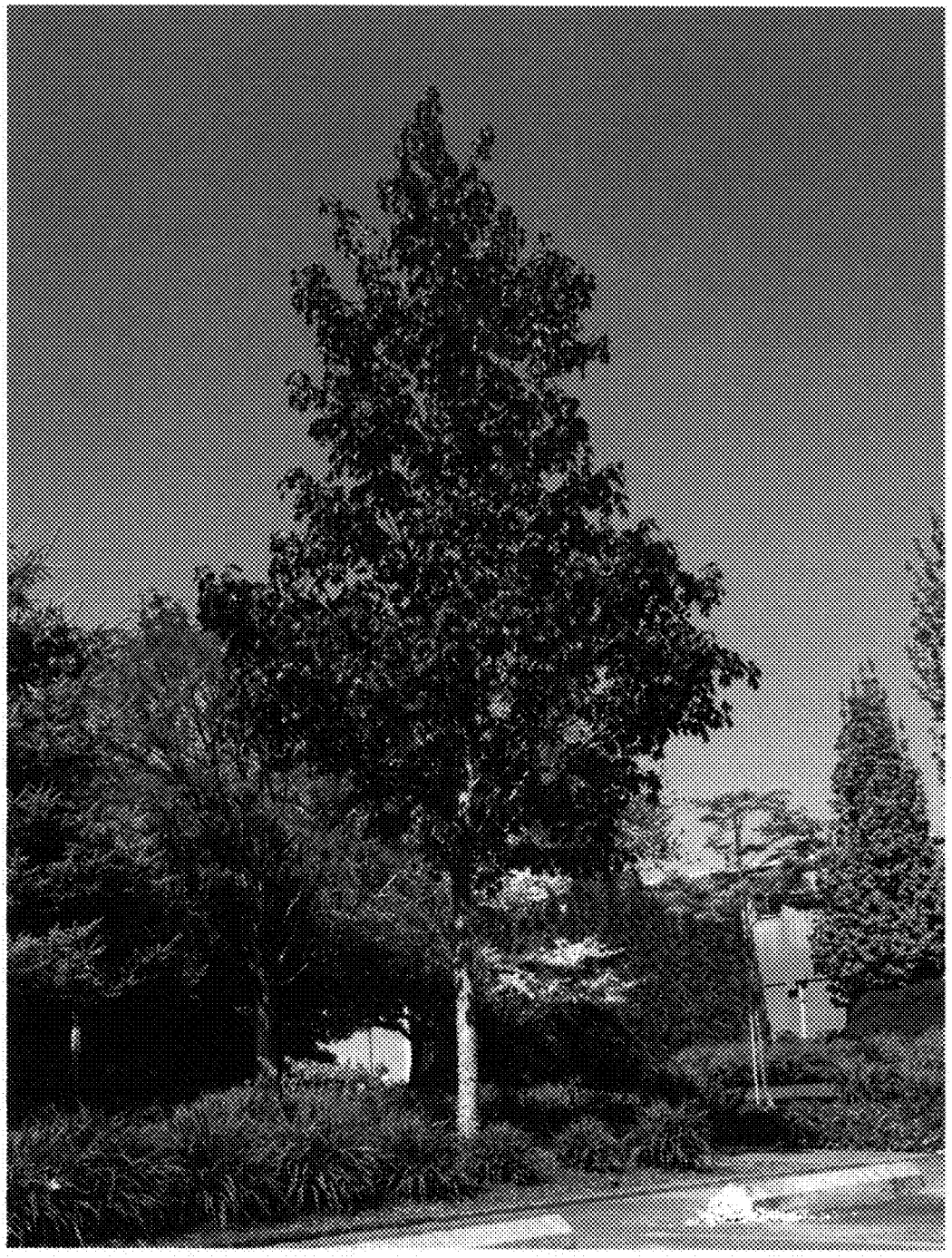
FIG. 1: Shows the original tree at 12 years of age in spring foliage and illustrates the color of the foliage and the moderately compact upright shape of the tree.
Figure 2:
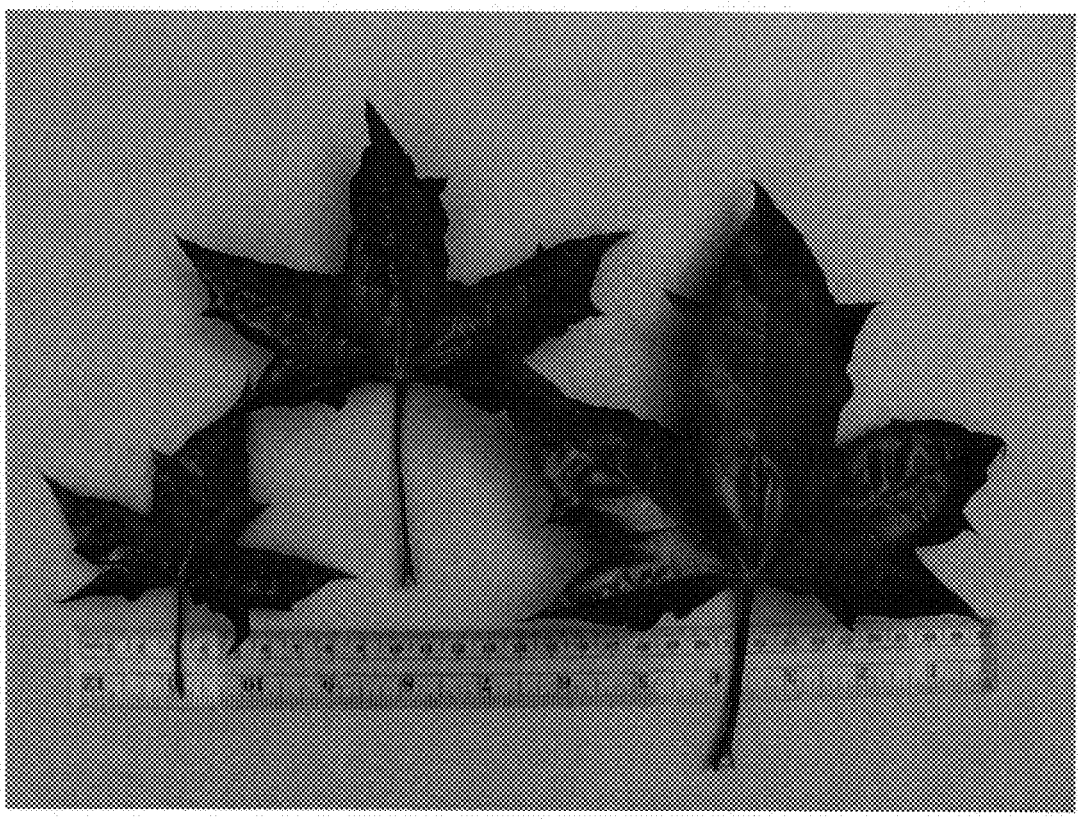
FIG. 2: Shows the upper surface of the summer leaves from my new tree illustrating the deep purple color with a minor green tint as well as the leaf shape.
Figure 3:
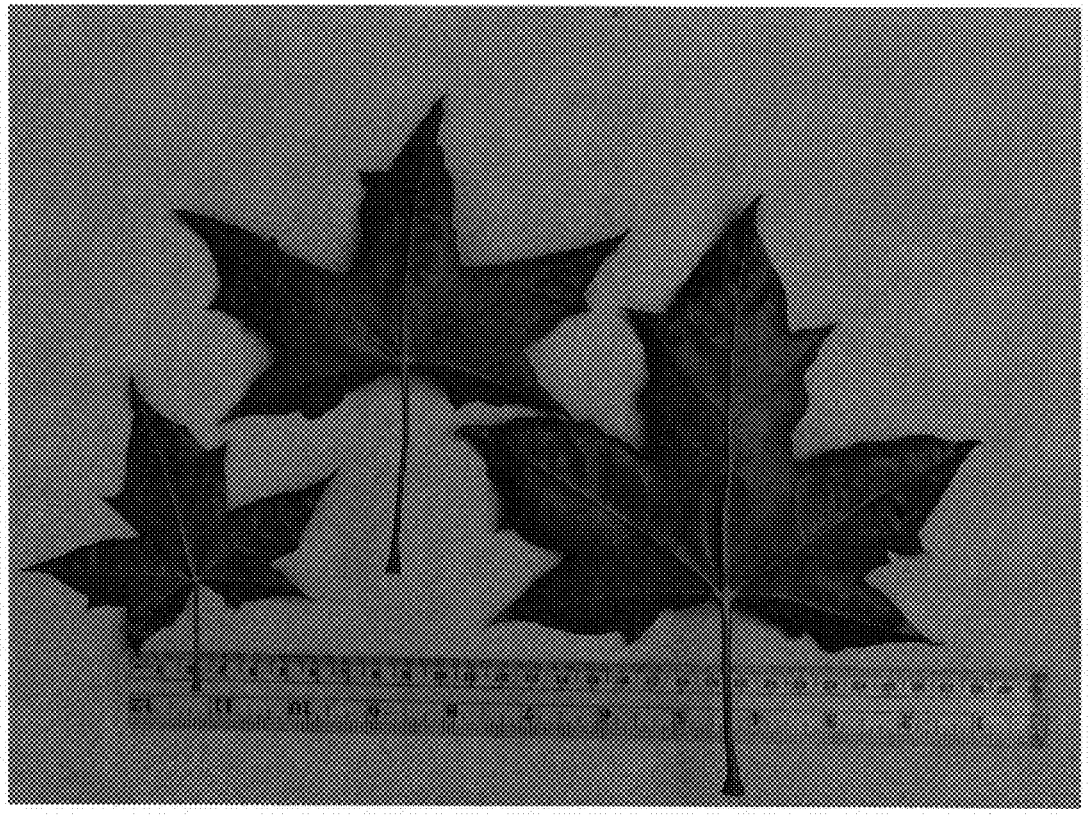
FIG. 3: Shows the lower surface of summer leaves from my new tree illustrating the distribution of purple and green coloration and showing the prominent leaf veins.
Figure 4:
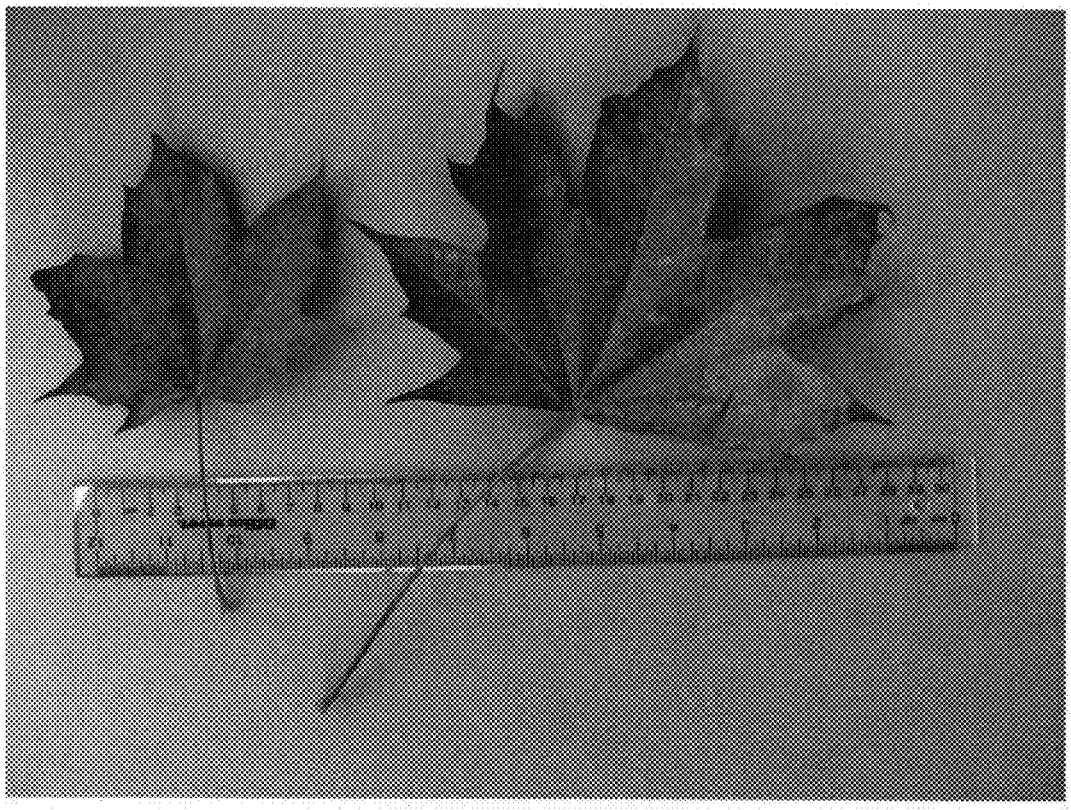
FIG. 4: Shows the fall coloration of the upper surface of leaves from my new tree.
Figure 5:
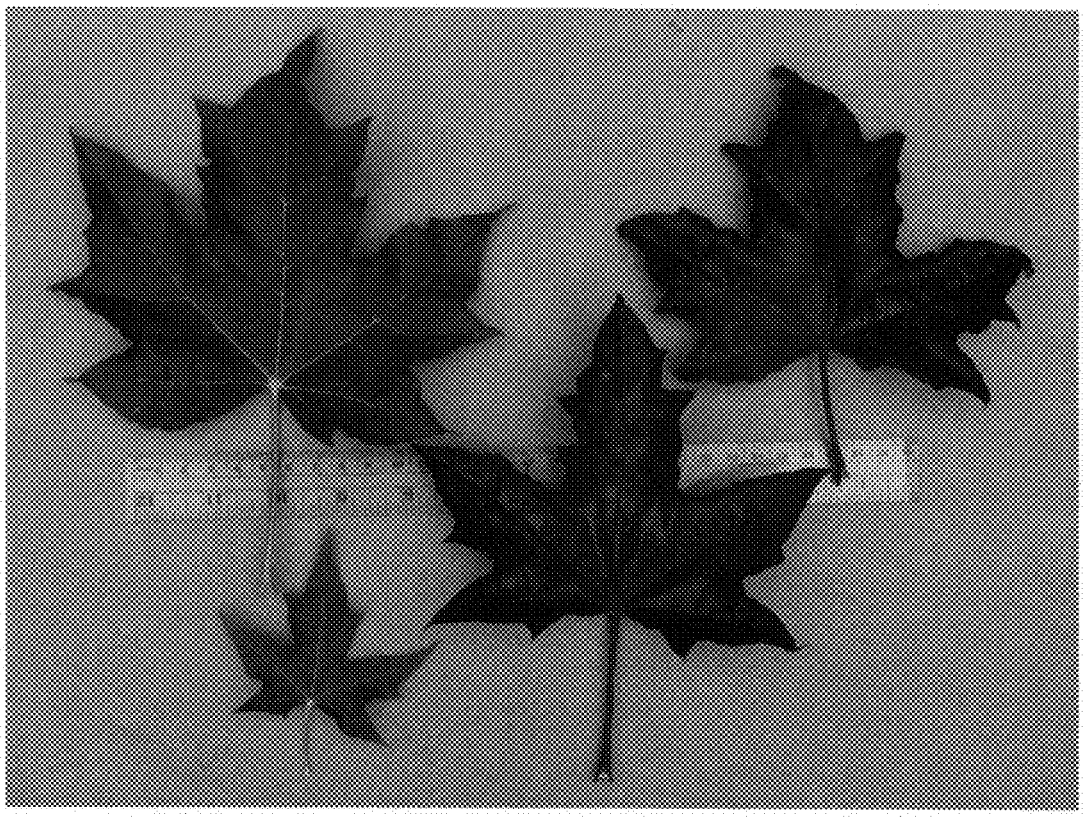
FIG. 5: Compares a leaf from a 'JFS-KW202' tree (lower right), a leaf from an *Acer truncatum* seedling tree (lower left), a leaf of an *Acer platanoides* tree (upper left); and a leaf of an *Acer platanoides* 'Crimson King' tree (U.S. Plant Pat. No. 735) upper right.
Figure 6:
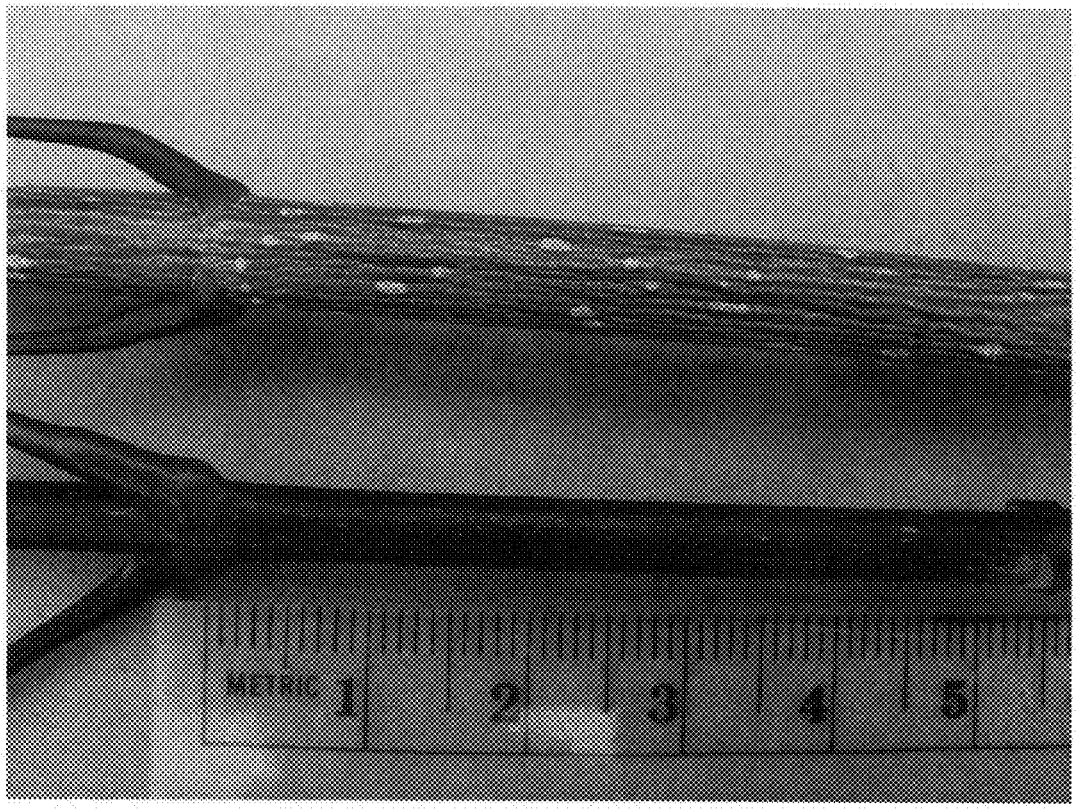
FIG. 6: Shows sections of a one year old branch of my new variety illustrating the smooth purple coloration of the young branch section and the striated appearance and lenticels on the larger, more mature branch section.
Figure 7:
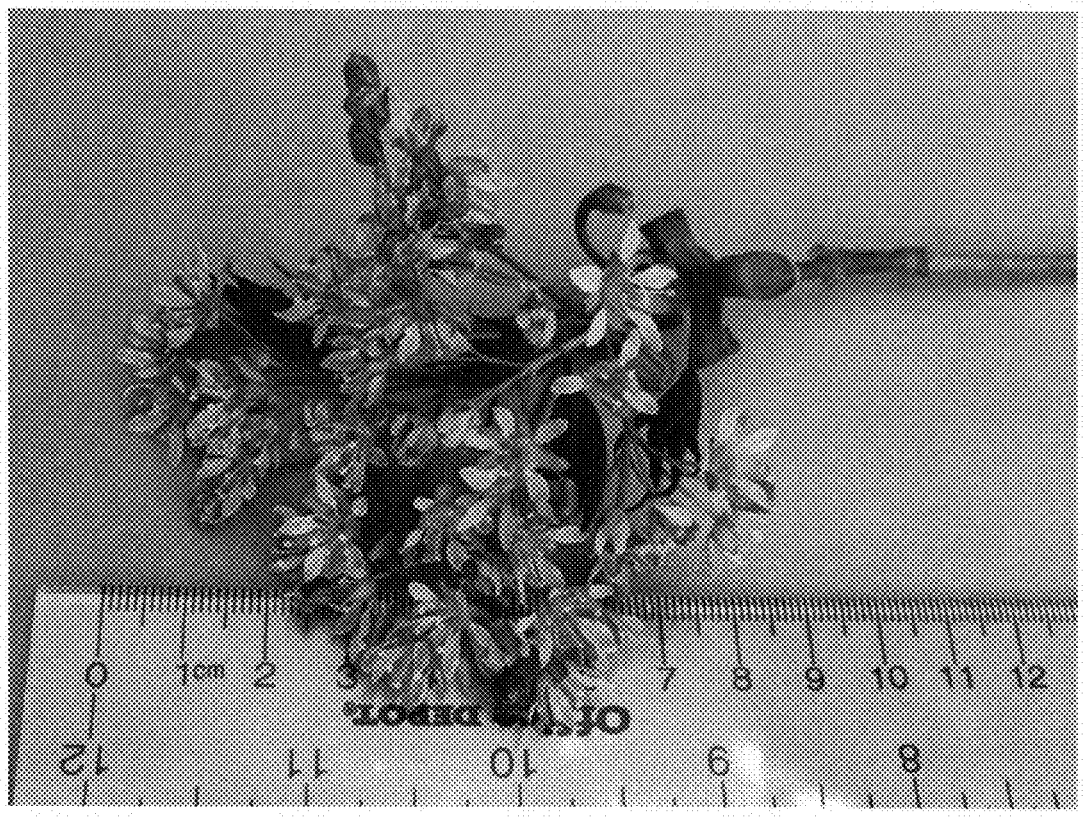
FIG. 7: Shows a corymb of flowers of my new variety.
Figure 8:
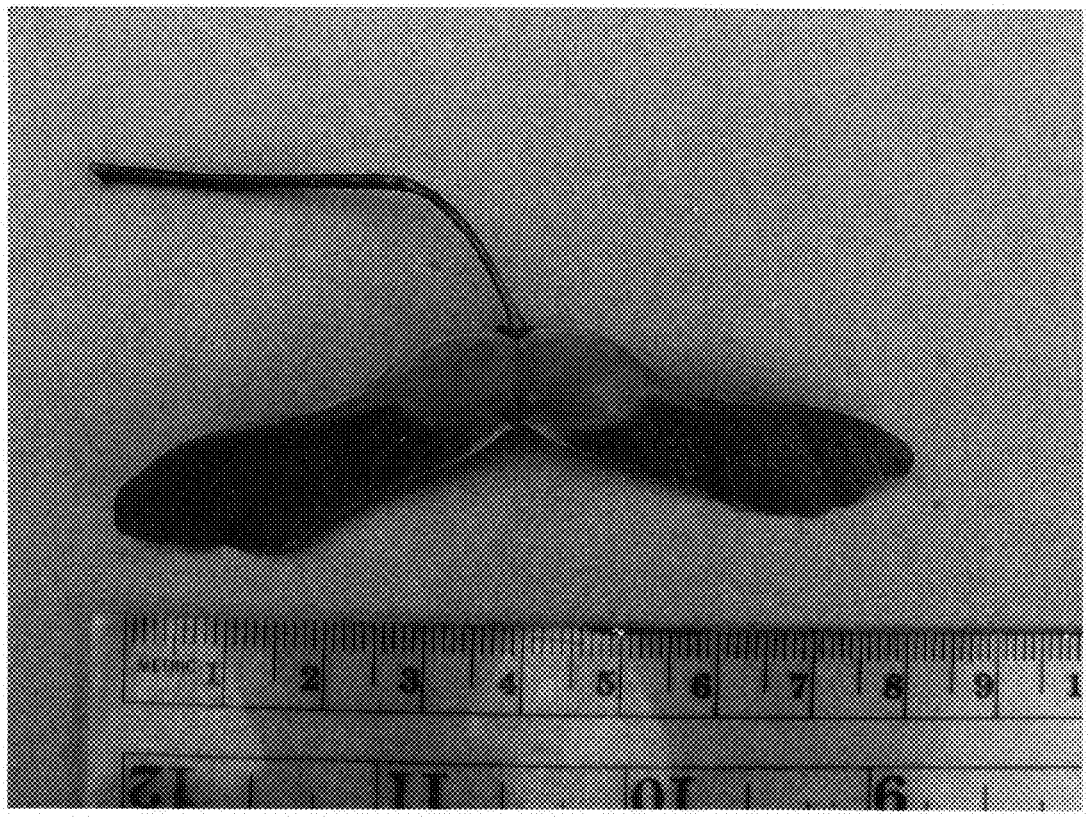
FIG. 8: Shows a pair of samaras at peak coloration as seeds are maturing on my new tree.
Figure 9:
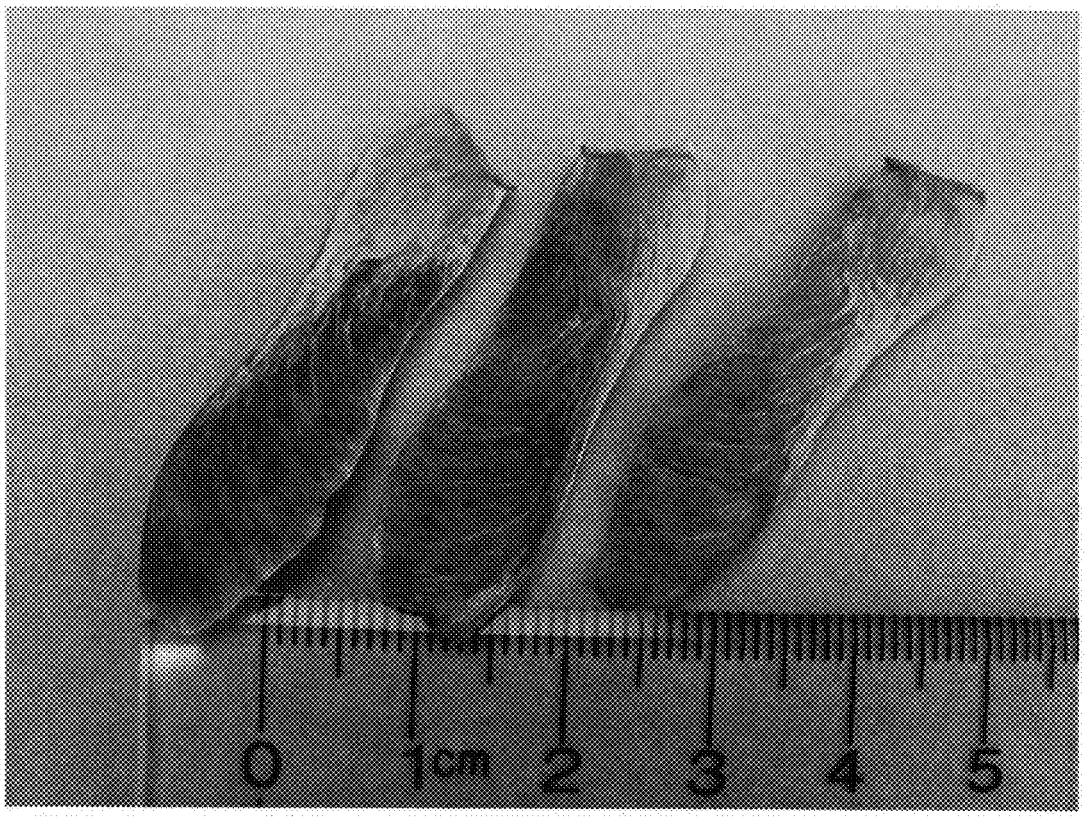
FIG. 9: Shows individual samaras when fully mature and dry at the time they fall from the tree.
Figure 10:
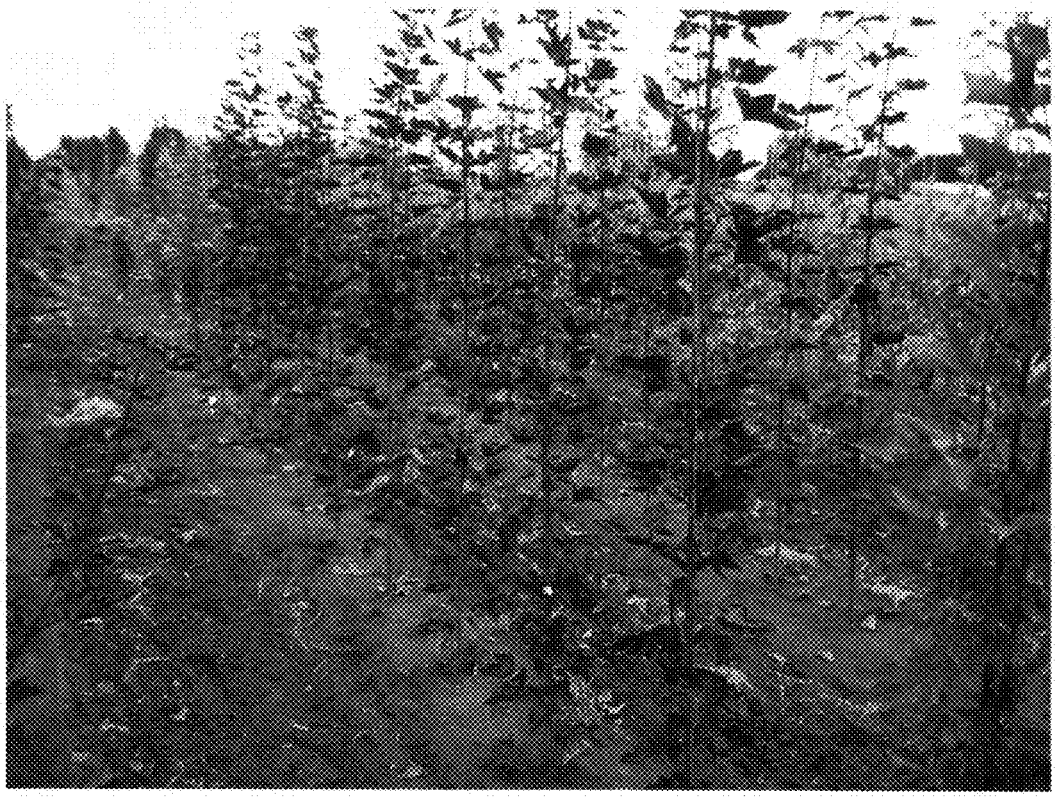
FIG. 10: Shows one year old budded trees in a nursery row illustrating the straightness of growth and generally unbranched trunk.
Figure 11:
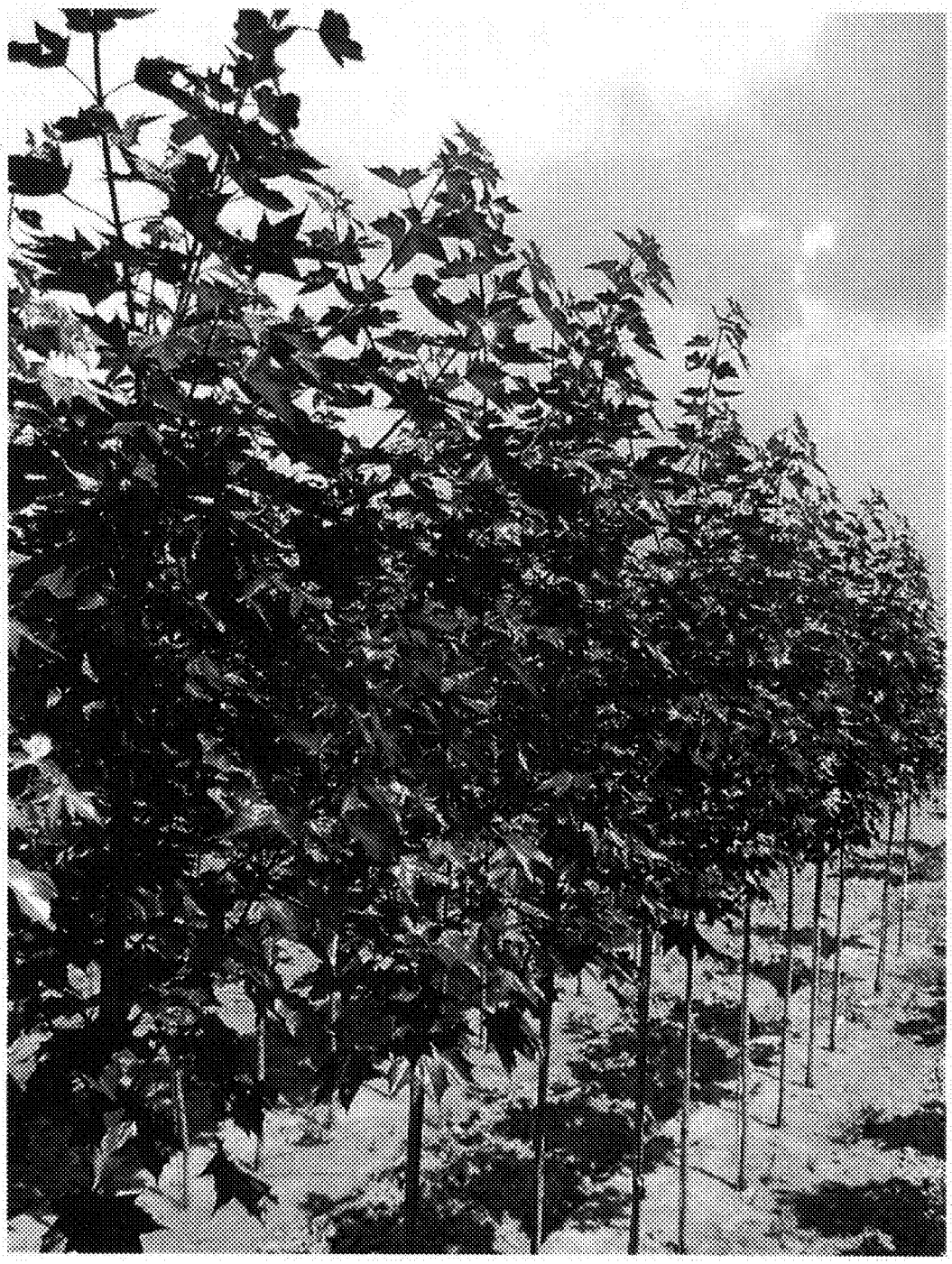
FIG. 11: Shows two year old trees in a nursery row illustrating the bright color of the new spring growth and the moderately dense and compact shape.

The following detailed description of the 'JFS-KW202' variety, with color terminology in accordance with The Royal Horticultural Society (R.H.S.) Colour Chart published by The Royal Horticultural Society in London © 2001, and is based on observations of the original tree and one, two, and three year old progeny. The observed progeny were trees which were growing in Boring, Oreg. and Canby, Oreg. Four year old progeny were heat tested in Hawkinsville, Ga. and cold tested in Madison, Ohio.

Scientific name: *Acer truncatum* 'JFS-KW202'.

Parentage:

*Seed parent.*—*Acer truncatum.*

*Pollen parent.*—Unknown.

Tree:

*Overall shape.*—Upright oval, with a dense and slightly compact branch structure.

*Height.*—8.1 meters at 12 years of age.

*Width.*—3.6 meters at 12 years of age.

*Caliper.*—13.4 cm at 30 cm above ground, 12.3 cm at 1 meter above ground, of 12 year old tree.

*Trunk.*—Sturdy, upright, strong and straight.

*Trunk bark texture.*—Smooth until approximately 8 years of age, then slightly roughened with very slight vertical furrows developing with greater age.

*Trunk bark color.*—Immature bark color: Greyed-orange 177A to Grey-brown 199B on two year old bark. Mature bark color: Greyed-green 197A to Grey-brown 199C, with colors tending to appear striated, following the slight vertical furrows on 12 year old trunk. Lenticels: Greyed-orange 164D to 165C. Rounded to oblong, 1 mm on first year wood, becoming 2 mm by 3 mm in the second year, then fading and disappearing by the fourth year.

*Primary branches.*—Sturdy, with primary branches diverging from the central trunk at 30° to 60° degree angles; with average branch angle being 45°.

*Branch color.*—The branch color changes over time for the first three years. In the first year, the bark begins with a smooth surface, Greyed-purple 187A, then as the season progresses it becomes striated with Greyed-orange 178A and 174B. In the second season, the branches are similar to Greyed-orange 177A. In the third season, the branches become Greyed-orange 177B to Grey-brown 199B.

*Branch lenticels.*—Greyed-orange 164D. Rounded to oblong, 1 mm, then expanding to 2 by 3 mm in the second year, then fading and disappearing as bark matures after approximately four years.

*Dormant buds:* 4 to 6 mm, ovoid with overlapping scales. Greyed-red 178A to Greyed-purple 183A.

*Internodes.*—5 to 10 centimeters, averaging 7.8 centimeters.

*Hardiness.*—USDA zone 6 or colder.

*Disease resistance.*—Similar to the species.

Leaves: Except as otherwise noted, observations are from twenty vigorous growth leaves.

*Arrangement.*—Opposite.

*Texture.*—Smooth.

*Sheen.*—Glossy.

*Length.*—7 cm to 20 cm, averaging 16.0 cm.

*Width.*—10 cm to 21 cm, averaging 14.6 cm.

*Petioles.*—6 cm to 10 cm long by 2 mm thick.

*Overall shape.*—Palmate, with 5 major lobes.

*Margin.*—Smooth between lobe tips.

*Tip.*—Primary leaf tip is acuminate, other lobe tips are acute.

*Base.*—Truncate to slightly cordate.

*Stipules.*—None.

*Spring leaf color, first emerging leaves.*—Greyed-purple 187A.

*Summer leaf color.*—Upper leaf surface: Greyed-purple 187A overall, but with a very slight cast of Yellow-green 147A in the central portion of the leaf. Lower leaf surface: Greyed-purple 183A overall, with a moderate cast of Yellow-green 147A in central portion of the leaf Vein: Prominent and protruding from the lower surface of the leaf, palmate: Mostly flush with the upper leaf surface.

*Fall leaf color.*—Fall color is a mix of Greyed-orange 169A, Greyed-orange 173B, Greyed-red 179A, and Greyed-purple 184A. Fall color typically starts on October 20, peaks on October 29, and ends with defoliation on November 5 under Boring, Oreg. growing conditions.

*Pubescence.*—Glabrous.

*Persistence.*—Tree is deciduous.

Flowers:

*Overall.*—Perfect, in many flowered erect to semi-erect corymbs, typically 40 to 60 flowers per corymb, opening just before the leaves.

*Shape.*—Symmetrical, cup shaped.

*Size.*—Corymb, 6 to 10 cm tall by 6 to 10 cm wide. Individual flowers 8 to 12 mm wide by 5 to 7 mm deep.

*Flower buds.*—Ovoid.

*Color.*—Unopened buds: Greyed-purple, 184A to 184B. Opened flower: Yellow 11A to Yellow-green 154C, with slight tints of Greyed-purple 183B on the backs of petals and sepals.

*Petals.*—Oblong with rounded tips, average size 5 mm long by 2 mm wide.

*Sepals.*—Oblong with bluntly obtuse to slightly obcordate tip, average size 4 mm long by 2 mm wide.

*Stamens.*—Typically 8 per flower, around perimeter of receptacle. Length averages 3 mm.

*Anthers.*—Average length 1 mm. Color Yellow 12A.

*Pistil.*—Short, averages 1 mm long, divides into a double stigma. Red, 46B at the base to Greyed-purple 185A at the tip of stigma.

*Pollen.*—Yellow-orange 16C.

*Pedicel.*—Length, 1 to 3 cm. Width 0.5 to 1 mm. Color, Yellow-green 153C to Greyed-purple 184A depending on sun exposure.

*Pubescence.*—None.

*Fragrance.*—None.

*Flowering date.*—In Boring, Oreg., 2009 season data: First bloom: April 20. Peak bloom, April 25. End of bloom: April 29.

Fruit: Observations are from a sampling of typical fruit.

*Type.*—Winged samara, with samaras held pendulously in pairs, joined at seed end, wings forming a 110 to 160 degree angle.

*Size.*—35 mm to 44 mm long by 9 to 13 mm wide.

*Shape.*—Oblong to oblancelote.

*Skin.*—Dry, slightly rough, with minutely raised striations on the wing. Glabrous.

*Lenticels.*—None.

*Color.*—Samaras become brighter as they ripen, then fade in color as they dry and fall from tree. At peak color: Greyed-purple 187A with leading edge of wing Yellow-green 147B to 148B. As the samara dries it gradually becomes more brown in color, similar to Greyed-orange 174A to 164B.

*Seeds.*—One per samara. A flattened broadly ovoid nutlet, typically 6 mm×7 mm×2 mm thick, Greyed-orange 166D.

*Stalk.*—Holding samaras where joined at the seed end, 2 cm to 5 cm long by 1 mm thick. Greyed-purple 187A with some tints of Yellow-green 147B.

*Fruit production.*—Sparse.

Comparison to other varieties:

My new variety differs from all existing varieties of *Acer truncatum* known to the inventor in that the color of its fully expanded summer leaves is Greyed-purple 187A (upper leaf surface) while all other named cultivars of *Acer truncatum* have summer leaves that are various shades of green, or variegated green and white. This includes 'Warrenred' U.S. Plant Pat. No. 7,433, 'Keithsform' U.S. Plant Pat. No. 7,529, 'Fire Dragon' U.S. Plant Pat. No. 17,367, and 'WF-AT1' U.S. Plant Pat. No. 20,109.

In overall appearance, the most similar looking cultivar in the nursery trade is a purple foliaged cultivar of a different species, *Acer platanoides* 'Crimson King' U.S. Plant Pat. No. 735, which was patented as "Maple Tree" without a cultivar name. My new variety is distinguished from 'Crimson King', the most similar looking cultivar, in the following ways:

| Feature | 'JFS-KW202' | 'Crimson King' |
|---|---|---|
| Height, 1 year trees | Shorter, 231 cm | Taller, 267 cm |
| Internode length, 1 year trees | Shorter, 7.8 cm | Longer, 12 cm |
| Leaf margin | Smooth between lobe points | Wavy between lobe points |
| Leaf gloss | Glossy | Satiny |
| Heat tolerance, central Georgia | Tolerant, grows well | Stressed, grows poorly |

Comparison to the parent species:

My new variety has purple colored summer foliage, Greyed-purple 187A, while the parent species *Acer truncatum* has green summer foliage, typically Yellow-green 144A to 147A, with all color measurements referring to the upper leaf surface of full expanded summer foliage.

The following table compares the differences of my new variety with the parent species, *Acer truncatum*, as well as with the similar species *Acer platanoides*:

| Feature | JFS-KW202 | *Acer truncatum* | *Acer platanoides* |
|---|---|---|---|
| Leaf width | 14.6 cm | 9.0 cm | 16.2 cm |
| Leaf length | 16.0 cm | 9.8 cm | 20.5 cm |
| Leaf surface sheen | Glossy | Glossy | Dull |
| Leaf color, summer upper surface | Greyed-purple 187A | Yellow-green 144A to 147A | Green 137B to 139B |
| Internode length | 8.0 cm | 4.1 cm | 11.6 cm |

I claim:

1. A new and distinct variety of maple tree that combines deep purple summer foliage with a slightly compact, upright growth habit and improved heat resistance in comparison to other maple trees with purple colored summer foliage.

* * * * *